United States Patent [19]

Wideman et al.

[11] 3,937,745

[45] Feb. 10, 1976

[54] SELECTIVE HYDROGENATION OF CYCLOPENTADIENE

[75] Inventors: Lawson G. Wideman, Akron; Henry R. Menapace, Stow, both of Ohio

[73] Assignee: The Goodyear Tire & Rubber Company, Akron, Ohio

[22] Filed: Aug. 29, 1974

[21] Appl. No.: 501,534

[52] U.S. Cl. .......................... 260/666 A; 252/431 C
[51] Int. Cl.$^2$ ..................... C07C 5/02; B01D 31/12
[58] Field of Search ................................ 260/666 A

[56] References Cited
UNITED STATES PATENTS 3,692,852  9/1972  Tabler............................ 260/666 A Primary Examiner—Delbert E. Gantz
Attorney, Agent, or Firm—F. W. Brunner; J. Y. Clowney

[57] ABSTRACT

There is disclosed a method of selective hydrogenation of cyclopentadiene which comprises contacting cyclopentadiene with hydrogen in the presence of a catalyst comprising aluminum trialkyl and organonickel compounds. The preferred solvent system for the hydrogenation process is an aliphatic alcohol.

6 Claims, No Drawings

SELECTIVE HYDROGENATION OF CYCLOPENTADIENE

This invention is directed to the selective hydrogenation of cyclopentadiene to cyclopentene. More specifically, it is directed to a process whereby cyclopentadiene is selectively hydrogenated to cyclopentene with the use of homogeneous catalyst system comprising soluble nickel compounds and aluminum trialkyls.

At the present time, substantial amounts of cyclopentadiene are available as a by-product from the steam cracking of naphtha to produce primarily ethylene. Cyclopentene has been found to be useful as a monomer for the formation of general purpose elastomers by ring opening polymerization of cyclopentene. Therefore, it is desirable to convert a portion of the excess cyclopentadiene into a more valuable raw material such as cyclopentene.

Therefore, it is an object of this invention to provide a method whereby cyclopentadiene can be converted, with relative ease, to high selectivities of cyclopentene.

It has been discovered that cyclopentadiene can be selectively hydrogenated to cyclopentene employing catalysts comprising (1) aluminum trialkyls and (2) organonickel salt.

The aluminum trialkyls employed in the catalyst of this invention may be represented by the formula $AlR_1R_2R_3$ wherein $R_1$, $R_2$ and $R_3$ are alkyl radicals including cycloalkyl radicals containing from 1 to 12 carbon atoms. Representative examples of such trialkyl aluminum compounds are aluminum trimethyl, triethyl, tri-n-propyl, triisopropyl, tri-n-butyl, triisobutyl, trihexyl, tricyclohexyl, trioctyl and tricyclooctyl.

The organonickel salts which are useful in the catalyst of this invention may be any nickel salt of a carboxylic acid or an organo complex compound of nickel. It is preferred to use a soluble nickel compound. The soluble nickel compounds are compounds of nickel with a mono- or a bi-dentate organic ligand containing up to 20 carbon atoms. The ligand is defined as an ion or a molecule bound to and considered bonded to the nickel atom. Mono-dentate means having one position through which covalent or coordinate bonds with the nickel may be formed; bi-dentate means having two positions through which covalent or coordinate bonds with the nickel may be formed. By the term soluble is meant that the nickel compounds are soluble in normal inert solvents such as aliphatic hydrocarbons, or aromatic hydrocarbons or alcohols. Thus, any nickel salt of a carboxylic acid containing from 1 to 20 carbon atoms may be employed. Representative of the organonickel compounds useful in this invention are nickel benzoate, nickel acetate, nickel naphthenate, nickel octoate, bis(α-furyl dioxime) nickel, nickel palmimate, nickel stearate, nickel acetylacetonate, nickel salicaldehyde, bis(salicaldehyde) nickel, ethylene diimine nickel, and nickel tetracarbonyl. Of these, the carboxylic acid salts of nickel are preferred.

The hydrogenation of the cyclopentadiene is straightforward and requires no special technique. Since the catlaysts employed are homogeneous, it is usually desirable to use a liquid phase hydrogenation.

It is usually desirable to utilize an inert solvent. The inert solvents are used as a heat transfer medium. Of the inert solvents which may be employed, the aromatic solvents represented by benzene, chlorobenzene and toluene and other aromatic solvents may be utilized. Aliphatic solvents represented by pentane, hexane, octane may be used. Cycloaliphatic solvents such as cyclohexane, and cyclopentane may be employed. Simple alcohols which are liquid at room temperature may also be employed. These alcohols are represented by methyl, ethyl, propyl, isopropyl, butyl, isobutyl, hexyl and octyl alcohols. Mixed alcohols may also be employed. Mixtures of all of these various solvents may be used. Of all of the solvents, it is preferred to employ aliphatic alcohols that are liquid at room temperature. Ethyl alcohol is the most preferred solvent to use. When a diluent or an inert solvent is employed, as has been indicated, they are employed as a heat transfer medium as well as a solvent. The ratio of cyclopentadiene to the solvent or diluent does not appear to be of great importance. It has been observed that a ratio of about 100 parts by weight of cyclopentadiene to about 1,000 volumes of solvent gives excellent results, both as a heat transfer medium and a solvent for the hydrogenation process.

When solvents which do not contain an active hydrogen are used, no particular techniques of mixing the catalyst components are required. The nickel compounds and the aluminum trialkyls can be mixed by either an in situ or a preform method. On the other hand, when an alcohol is to be used as the solvent system in the hydrogenation process, the catalyst components are premixed in small amounts of hydrocarbon solvent, preferably aromatic, before being added to the alcoholic cyclopentadiene mixture. This technique is required because of the highly reactive nature of aluminum trialkyls to the active hydrogens of the alcohols.

The reaction parameters at which the hydrogenation process of this invention is conducted do not seem to be extremely critical. The hydrogenation of cyclopentadiene to cyclopentene is exothermic and therefore the hydrogenation reaction can usually be initiated at room temperature or lower depending on the other reaction parameters. Because the hydrogenation process of this invention is exothermic, the process does not require a large heat input. Temperatures ranging from about 15°C up to temperatures of 100°C or slightly above have been sucessfully employed. It is usually desirable to operate at temperatures between about 25°C and about 60°C for purposes of economy.

The pressure of the hydrogen which is employed in the process of this invention likewise does not seem extremely critical. Pressures as low as about 100 pounds per square inch gauge (psig) are adequate. Hydrogen pressures above about 600 psig show no further advantage and therefore would be uneconomical. This is not to say, however, that pressures above 600 psig could not be employed.

The ratio of the trialkyl aluminum compound to the nickel compound (Al/Ni) have not been found to be critical. A mole ratio of Al/Ni of from about 1.5/1 to about 10/1 have been employed, but a mole ratio of Al/Ni of about 2/1 to about 6/1 is preferred.

The mole ratio of cyclopentadiene (CPD) to the catalyst in terms of CPD to nickel (Ni) may vary from a mole ratio of CPD/Ni from about 50 to about 3000 with from about 100 to about 1000 being preferred.

There is no lower limit of CPD/Ni if the solvent to the CPD mole ratio is increased. It has been determined that about 3,000 moles of CPD per mole of nickel is a practical catalyst concentration to employ.

The reaction parameters discussed above are not to be construed as absolute limits on the operating conditions of the hydrogenation of cyclopentadiene to cyclopentene employing the trialkyl aluminum compound and the nickel compound as a catalyst. Those skilled in the art will readily realize that if a higher concentration is employed, that a lower temperature may well be employed in a successful hydrogenation process. Likewise, if a higher hydrogen pressure is employed, a lower temperature as well as a lower catalyst concentration can be utilized. On the other hand, if the mole ratio of Al/Ni of the catalyst components is properly adjusted, to the optimum, the other reaction parameters such as catalyst concentration, hydrogen pressure, and temperature may be varied to give optimum conditions. Since all of the reaction parameters are operating conditions, work in concert, and each has an effect on the other, those skilled in the art can readily optimize the hydrogenation process and develop a set of operating conditions and reaction parameters which will give the most economic results. As a guideline, one might say that at an Al/Ni mole ratio of catalyst components of about 3/1 that hydrogen pressures of 600 psig would operate adequately at about 25°C. On the other hand, at hydrogen pressures of approximately 150 psig to have a relatively fast hydrogenation process would require temperatures in the neighborhood of about 50° or 60°C.

The process of the invention can further be ascertained by reference to the following specific embodiment which is intended to be representative rather than restrictive of the scope of this invention.

EXAMPLE I

A heat-dried, 1-liter stainless steel reactor was flushed with nitrogen and charged with an ethanolic solution (200 ml total volume) containing 20 g of freshly distilled cyclopentadiene. The reactor was then charged with a solution of the pre-mixed nickel catalyst that was formed by adding 3.0 mmol of nickel octanoate to 50 ml of sodium-dried benzene, followed by 6.0 mmol of Et$_3$Al under nitrogen. This being an Al/Ni mole ratio of 2/1 and a CPD to nickel mole ratio of 100/1. The reactor was held at room temperature and stirred for 20 minutes (time required for the calculated amount of hydrogen to saturate one double bond of the CPD to be taken up) at 600 psig H$_2$. The reactor was cooled and a sample of the reaction mixture was subjected to gas chromatographic analysis on a 50 ft ODPN column at room temperature with ethanol as the internal standard. The analysis revealed:
Cyclopentadiene conversion — 97.0%
Cyclopentene selectivity — 92.0%

EXAMPLE II

In a reactor such as that described in Example I, containing 20 grams of freshly distilled cyclopentene dissolved in 200 milliliters total volume of ethanol was added a solution of a pre-mixed catalyst formed from 3.0 millimoles of nickel octanoate and 6.0 millimoles of triethyl aluminum in 50 ml of benzene. These amounts gave an Al/Ni mole ratio of 2/1 and a CPD to Ni mole ratio of 100 to 1. In one of the runs, the temperature was maintained at 50°C and the initial hydrogen pressure was 150 psig. At the end of two minutes, which was the time required for the calculated amount of hydrogen to saturate one of the double bonds of the CPD to be taken up, the hydrogenation was stopped and a sample subjected to gas chromatographic analysis. This run resulted in a CPD conversion of 91.7 percent and a selectivity to cyclopentene of 89.0 percent.

In another identical run utilizing the same catalyst components but at a temperature which was controlled at 25°C, after 20 minutes the reaction was discontinued and the conversion of the cyclopentadiene was determined to be 92 percent and the selectivity to cyclopentene was 86 percent.

EXAMPLE III

In an example similar to that of Examples I and II except that 34 grams of cyclopentadiene was employed in 200 ml of total volume of ethyl alcohol and 0.5 m mols of nickel octanoate and 3.0 m mols of aluminum triethyl was employed. These amounts gave an Al/Ni mole ratio of 6/1 and a CPD/Ni mole ratio of 1000/1. The initial hydrogen pressure was 150 psig. The temperature was controlled at 60°C. and the hydrogenation was completed in less than ten minutes. The analysis of the product revealed that the cyclopentadiene conversion was 98.1 percent and the selectivity to cyclopentene was 90.8 percent.

While certain representative embodiments and details have been shown for the purpose of illustrating the invention, it will be apparent to those having skill in the art that certain changes and modifications may be made therein without departing from the spirit or scope of the invention.

What is claimed is:

1. In the method of selective hydrogenation of cyclopentadiene which comprises contacting cyclopentadiene with hydrogen and in contact with a homogeneous catalyst, the improvement which comprises utilizing as a homogeneous catalyst a mixture consisting of an aluminum trialkyl and an organonickel compound selected from the group consisting of nickel salts of carboxylic acids, nickel acetyacetonate, nickel salicaldehyde, bis(salicaldehyde) nickel, ethylene diamine nickel, bis($\alpha$-furyl dioxime) nickel and nickel tetracarbonyl in which the mole ratio of the trialkyl aluminum compound/nickel compound ranges from about 1.5/1 to about 10/1.

2. The method according to claim 1 in which an alcohol is employed as a solvent.

3. The method according to claim 1 in which the hydrogen pressure ranges from about 100 to about 600 psig.

4. The method according to claim 1 in which the nickel compound is a salt of a carboxylic acid.

5. The method according to claim 1 in which the mole ratio of cyclopentadiene to nickel ranges from 100 to 3000.

6. The method according to claim 1 in which ethyl alcohol is employed as a solvent, the mole ratio of aluminum trialkyl to the organonickel compound ranges from about 2/1 to about 6/1, the hydrogen pressure ranges from about 100 to about 600 psig, the mole ratio of the cyclopentadiene to nickel ranges from about 500 to about 1000 and in which the organonickel compound is a salt of a carboxylic acid.

* * * * *